(12) United States Patent
Eger et al.

(10) Patent No.: US 9,211,384 B2
(45) Date of Patent: Dec. 15, 2015

(54) RESPIRATOR OR ANESTHESIA SYSTEM

(75) Inventors: Marcus Eger, Lübeck (DE); Tobias Glaw, Lübeck (DE); Thomas Krüger, Reinfeld (DE); Hans-Ullrich Hansmann, Barnitz (DE)

(73) Assignee: Dräger Medical GmbH, Lübeck (DE)

( * ) Notice: Subject to any disclaimer, the term of this patent is extended or adjusted under 35 U.S.C. 154(b) by 1052 days.

(21) Appl. No.: 13/043,054

(22) Filed: Mar. 8, 2011

(65) Prior Publication Data

US 2011/0240021 A1    Oct. 6, 2011

(30) Foreign Application Priority Data

Mar. 30, 2010   (EP) .................................. 10 158 480

(51) Int. Cl.
| | | |
|---|---|---|
| *A61M 16/00* | (2006.01) | |
| *A61M 16/01* | (2006.01) | |
| *A61M 16/12* | (2006.01) | |
| *A61M 15/00* | (2006.01) | |
| *F16K 31/02* | (2006.01) | |
| *A62B 7/00* | (2006.01) | |
| *A61M 16/18* | (2006.01) | |
| *A61M 16/22* | (2006.01) | |
| *H02J 7/00* | (2006.01) | |

(52) U.S. Cl.
CPC .............. *A61M 16/01* (2013.01); *A61M 16/122* (2014.02); *A61M 16/18* (2013.01); *A61M 16/22* (2013.01); *A61M 2205/3561* (2013.01); *A61M 2205/8206* (2013.01); *A61M 2230/60* (2013.01); *A61M 2230/63* (2013.01); *H02J 7/0013* (2013.01); *H02J 7/0068* (2013.01)

(58) Field of Classification Search
CPC ..................... A61M 16/00; A61M 2016/0021; A61M 2016/0039; A61M 2016/0069; A61M 16/06; A61M 16/18; A61M 16/104; A61M 16/01
USPC .................... 128/203.14, 15, 202.16, 204.23, 128/204.18, 204.21; 328/108, 104
See application file for complete search history.

(56) References Cited

U.S. PATENT DOCUMENTS

| 5,353,788 | A | 10/1994 | Miles | |
|---|---|---|---|---|
| 6,238,338 | B1 * | 5/2001 | DeLuca et al. | ................ 600/300 |

(Continued)

FOREIGN PATENT DOCUMENTS

| AU | 707 148 B2 | 7/1999 |
|---|---|---|
| DE | 101 64 446 A1 | 7/2003 |

(Continued)

*Primary Examiner* — Tan-Uyen (Jackie) T Ho
*Assistant Examiner* — Mark Wardas
(74) *Attorney, Agent, or Firm* — McGlew and Tuttle, P.C.

(57) ABSTRACT

A respirator or anesthesia system for respirating a patient (20) includes a gas delivery device (3); at least one gas line (4) for forming a breathing air line system, especially a breathing air circulation system; at least one EMG sensor for detecting the electromyographic muscle activity of the respiratory muscles of a patient (20) being respirated; and a control (9) for controlling and/or regulating the output of the gas delivery device (3) as a function of the detected muscle activity of the respiratory muscles. An adaptation of the part of respiration to the performance capacity of the respiratory muscles of the patient (20) being respirated is made possible without invasive measurement of the electromyographic activity of the respiratory muscles by the at least one EMG sensor being an sEMG sensor (6).

10 Claims, 7 Drawing Sheets

(56) References Cited

U.S. PATENT DOCUMENTS

| | | | |
|---|---|---|---|
| 2004/0015096 A1* | 1/2004 | Mok et al. | 600/547 |
| 2005/0115561 A1* | 6/2005 | Stahmann et al. | 128/200.24 |
| 2006/0152197 A1* | 7/2006 | Stanesti et al. | 320/135 |
| 2007/0163588 A1 | 7/2007 | Hebrank et al. | |
| 2008/0308104 A1* | 12/2008 | Blomberg et al. | 128/204.23 |
| 2010/0113945 A1* | 5/2010 | Ryan | 600/486 |
| 2011/0074342 A1* | 3/2011 | MacLaughlin | 320/108 |
| 2011/0126829 A1* | 6/2011 | Carter et al. | 128/202.22 |

FOREIGN PATENT DOCUMENTS

| | | |
|---|---|---|
| DE | 102007062214 B3 | 8/2009 |
| WO | WO 98/48877 A1 | 11/1998 |
| WO | WO 2006131149 A1 | 12/2006 |

\* cited by examiner

RESPIRATOR OR ANESTHESIA SYSTEM

CROSS REFERENCE TO RELATED APPLICATIONS

This application claims the benefit of priority under 35 U.S.C. §119 of European Patent Application EP 10 158 480.3 filed Mar. 30, 2010, the entire contents of which are incorporated herein by reference.

FIELD OF THE INVENTION

The present invention pertains to a respirator (also known as a ventilator) or anesthesia system, for respirating (also known as ventilation) a patient, with a gas delivery means at least one gas line for forming a breathing air line system, especially a breathing air circulation system, at least one electromyographic (EMG) sensor for detecting the electromyographic muscle activity of the respiratory muscles of a patient being respirated and a control means for controlling and/or regulating the output of the gas delivery means. The invention also relates to a process for controlling and/or regulating a respirator or anesthesia system, including delivering breathing air through at least one gas line of a breathing air line system with a gas delivery means, detecting the electromyographic muscle activity of the respiratory muscles of a patient being respirated and controlling and/or regulating the output of the gas delivery means and/or the pressure of the inspiration air.

BACKGROUND OF THE INVENTION

Respiration of patients is necessary for various medical applications, e.g., during surgical procedures. Respirators or anesthesia systems are used to respirate patients and can additionally also be used as anesthesia apparatuses or anesthesia systems for anesthesia with an anesthetic reflector and anesthetic dispensing unit. The expiration gas expired by the patient can be reused at least partly as an inspiration gas in some respirator or anesthesia systems, i.e., these systems represent a rebreathing system with a breathing air circulation system. A gas delivery means, which sends the breathing air to the patient during the inspiration, is present in the respirator with the breathing air circulation system. The gas delivery means is either switched off or is operated with a very small delivery flow only during and after the expiration.

The respiration performed by the respirator or anesthesia system may either fully take over the patient's own breathing activity or replace the patient's own breathing activity only partly in case of an assisting method, so that the patient's respiratory muscles take over part of the respiratory activity. Control of part of the respiration is necessary for improved therapy, especially in chronic obstructive pulmonary disease (COPD) patients, i.e., the part of the patient's own respiratory activity can be controlled and/or regulated. The output of the gas delivery unit of the respirator or anesthesia system is to be controlled for this and the point in time of respiration and the amplitude of respiration are to be adapted to the patient's own respiration. The electromyographic activity of the patient is detected for this invasively with electromyographic sensors (EMG sensors). The EMG sensors are arranged at the patient invasively, especially in the trachea.

DE 10 2007 062 214 B3 shows a process for automatically controlling a respirator for ventilation to be assisted proportionally with a control means and with a fan, which delivers a breathing gas with a pressure preset by the control unit. An electric signal is recorded electromyographically with electrodes and the breathing activity and respiratory muscle pressure are determined from this.

SUMMARY OF THE INVENTION

The object of the present invention is therefore to make available a respirator or anesthesia system and a process for controlling and/or regulating a respirator or anesthesia system, in which adaptation of the part of respiration to the performance capacity of the respiratory muscles of the patient being respirated is possible without invasive measurement of the electromyographic activity of the respiratory muscles.

This object is accomplished with a respirator or anesthesia system for respirating a patient, comprising a gas delivery means, at least one gas line for forming a breathing air line system, especially a breathing air circulation system, at least one EMG sensor (electromyographic sensor) for detecting the electromyographic muscle activity of the respiratory muscles of a patient being respirated, a control means for controlling and/or regulating the output of the gas delivery means as a function of the detected muscle activity of the respiratory muscles, wherein the at least one EMG sensor is an a surface electromyographic sensors (sEMG). The sEMG is consequently a surface EMG sensor and detects the electric activity of the respiratory muscles noninvasively, i.e., on the surface, especially on the skin surface, of the patient. Invasive measurement of the electric activity of the respiratory muscles, for example, in the trachea, in an invasive manner with an EMG sensor, which is unpleasant or harmful to the patient, is thus advantageously no longer necessary. The beginning of the patient's breathing phase and/or the own breathing activity or the patient's own breathing can thus be detected noninvasively with the at least one sEMG sensor.

In an additional variant, the respirator or anesthesia system is provided with a means, e.g., at least one button and/or a lever, for controlling and/or regulating and/or changing the part of the respiration. A physician can thus increase and reduce the part of the respiration and thus adapt it to the patient's health status, for example, for slowly weaning the patient from respiration. Increasing the respiration leads to a reduction of the patient's own breathing and vice versa.

The respirator or anesthesia system preferably comprises at least two sEMG sensors, especially a pair of sEMG sensors.

In an additional embodiment, the respirator or anesthesia system comprises at least one measuring module, and the at least one sEMG sensor is arranged at the at least one measuring module.

The at least one sEMG sensor is preferably arranged at a distance of less than 100 cm, 70 cm, 50 cm, 30 cm, 20 cm or 10 cm from the measuring module.

In another embodiment, the at least one sEMG sensor has an analog cable or is connected by a wireless connection with the at least one measuring module. The voltage from the respiratory muscle activity measured by the at least one sEMG sensor, preferably on the skin surface, is sent with the analog cable to the at least one measuring module. Very low voltages in the range of a few $\mu V$ up to about 100 $\mu V$ are now measured by the at least one sEMG. The measured voltage is thus converted into digital signals in the at least one sEMG sensor and transmitted into the measuring module and/or main unit.

In an additional embodiment, the respirator or anesthesia system has a main unit with a main housing and with the gas delivery means and the at least one measuring module is a preferably portable assembly unit separate from the main unit.

In one variant, the at least one measuring module is provided with an analog-digital conversion unit for converting the analog electromyographic muscle activity detected by the at least one sEMG sensor into digital signals. The at least one sEMG sensor detects only very low voltages from the respiratory muscles, so that these very low voltages may become distorted when sending these very low currents to the main unit over a greater distance. Conversion of these very low measured voltages into digital signals is meaningful and effective for this reason in case of a locally close-range conversion in the analog-digital conversion unit in the at least one measuring module.

The at least one measuring module preferably has a data processing unit and/or an energy supply unit.

In one variant, the supply unit is at least one battery, preferably a plurality of batteries, and/or a capacitor, preferably a plurality of capacitors, as an energy storage means.

In another embodiment, the main unit is provided with a charging unit for the at least one energy storage means.

In an additional embodiment, the energy supply unit in the at least one measuring module is at least one power cable and the at least one power cable is led to the main unit for sending electric current from the main unit to the at least one measuring module, and the current sent by the at least one power cable can preferably be sent at the main unit from the main unit to the at least one power cable by means of induction with an induction unit with two coils. The current is transmitted in the induction unit by a primary coil by means of induction to a secondary coil and the measuring module is thus electrically and/or magnetically uncoupled from the main unit.

In particular, the induction unit is arranged in or at the main unit.

In another embodiment, the respirator or anesthesia system is provided with at least two energy storage means, especially a battery or a capacitor, and with a charging and switching unit for supplying the at least one measuring module with energy, so that the at least one energy storage means is electrically separated from the energy supply of the main unit and is electrically connected to the measuring module during the phase of discharge of the at least one energy storage means, and the at least one energy storage means is electrically separated from the at least one measuring module and is electrically connected to the main unit during a phase of charging of the at least one energy storage means. The at least one measuring module is thus electrically and/or magnetically uncoupled from the main unit because the at least one measuring module is not connected simultaneously directly to the main unit by means of an electric cable.

The at least one measuring module is associated with at least one MMG sensor (mechanomyographic sensor) and/or to at least one acceleration sensor and/or to a microphone in an additional embodiment for the non-invasive detection of the muscle activity of the respiratory muscles, so that these sensors are non-invasive sensors. The at least one MMG sensor (mechanomyographic sensor) and/or the at least one acceleration sensor and/or the microphone is connected to the measuring module by means of an analog cable analogously to the at least one sEMG sensor.

The output of the gas delivery means and/or the pressure of the inspiration gas can be preferably controlled and/or regulated as a function of the data and/or currents of the at least one MMG sensor and/or of the at least one acceleration sensor and/or of the microphone.

A process according to the present invention is provided for controlling and/or regulating a respirator or anesthesia system, especially a respirator or anesthesia system described in this patent application, with the steps of delivering breathing air through at least one gas line of a breathing air line system with a gas delivery means; detecting the electromyographic muscle activity of the respiratory muscles of a patient being respirated, preferably with an EMG sensor; controlling and/or regulating the output of the gas delivery means and/or the pressure of the inspiration air as a function of the muscle activity of the respiratory muscles, which is to be detected, wherein the electromyographic muscle activity is detected by at least one sEMG sensor on the skin surface of the patient being respirated.

The analog electromyographic muscle activity detected by the at least one sEMG sensor is converted into digital signals in an additional embodiment. The sEMG sensor detects as the analog muscle activity a very low voltage of the respiratory muscle.

At least one measuring module with at least one sEMG sensor is preferably supplied with electric energy from a main unit of the respirator or anesthesia system.

In another embodiment, the electric energy is sent through at least one power cable from the main unit to the at least one measuring module and the current is now transmitted, preferably at the main unit, by induction to reduce the coupling capacity between the at least one measuring module and the main unit (the at least one measuring module is thus electrically and/or magnetically uncoupled from the main unit, because current can be sent from the main unit to the at least one measuring module by means of induction only) and/or at least one energy storage means is arranged at the at least one measuring module and the at least one measuring module is brought to the main unit after detection of the electromyographic muscle activity with the at least one measuring module at the patient, and the at least one energy storage means is charged at the main unit and at least one other measuring module is preferably brought to the patient after charging the at least one energy storage means at the main unit for detecting the electromyographic muscle activity (the at least one measuring module is thus electrically and/or magnetically uncoupled from the main unit, because the energy storage means is charged only when the energy storage means is not connected electrically to the measuring module but to the main unit only) and/or the at least one measuring module is supplied with electric energy by means of at least two energy storage means, and the at least one measuring module is supplied with electric energy during a phase of discharge of at least one energy storage means and the at least one energy storage means is electrically separated from the main unit during the phase of discharge of the at least one energy storage means, and/or the at least one energy storage means is charged with electric energy from the main unit during a phase of charging of the at least one energy storage means, and the at least one energy storage means will be and/or is electrically separated from the at least one measuring module during a phase of charging (the at least one measuring module is thus electrically and/or magnetically uncoupled from the main unit, because the energy storage means is charged only when the energy storage means is not connected electrically to the measuring module but to the main unit only).

In another embodiment, the digital data on the muscle activity of the respiratory muscles is transmitted from the at least one measuring module to the main unit in a wireless manner (with a wireless connection) or in a wired manner.

In another embodiment, a coupling capacity between the at least one measuring module and the main unit is lower than 40 pF to 50 pF, preferably lower than 30 pF to 40 pF, and especially lower than 10 pF to 12 pF (pFarad).

In an additional variant, the main unit of the respirator or anesthesia system has a $CO_2$ absorber. The carbon dioxide is extracted from the expiration gas expired by the patient being respirated by the $CO_2$ absorber.

The respirator or anesthesia system preferably has an inspiration tube and an expiration tube.

In another variant, the respirator or anesthesia system has a Y-piece or a breathing mask.

In an additional variant, the inspiration tube and/or expiration tube is connected at the Y-piece or at the breathing mask.

A nonreturn valve each is preferably arranged at the inspiration tube and expiration tube.

In an additional embodiment, the main unit of the respirator or anesthesia system has an anesthetic reflector. The anesthetic, e.g., halothane or enflurane, is extracted from the expiration gas by means of the anesthetic reflector and the extracted anesthetic is fed to the inspiration gas.

In an additional embodiment, the main unit of the respirator or anesthesia system has an anesthetic dispensing unit with an anesthetic reservoir. Anesthetic is added to the inspiration gas by means of the anesthetic dispensing unit. The anesthetic is, in general, in the liquid form and the anesthetic is converted from the liquid into the gaseous form in the anesthetic dispensing unit and is thus fed to the patient.

In the embodiment of a breathing air circulation system, the expiration gas expired by the patient is fed at least partly to the patient again as an inspiration gas. The carbon dioxide is extracted from the expired expiration gas, preferably in the $CO_2$ absorber, and the inspiration gas to be fed to the patient is preferably enriched with a mixture of oxygen, laughing gas, air and/or xenon in a gas mixer.

Exemplary embodiments of the present invention will be described in more detail below with reference to the drawings attached. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
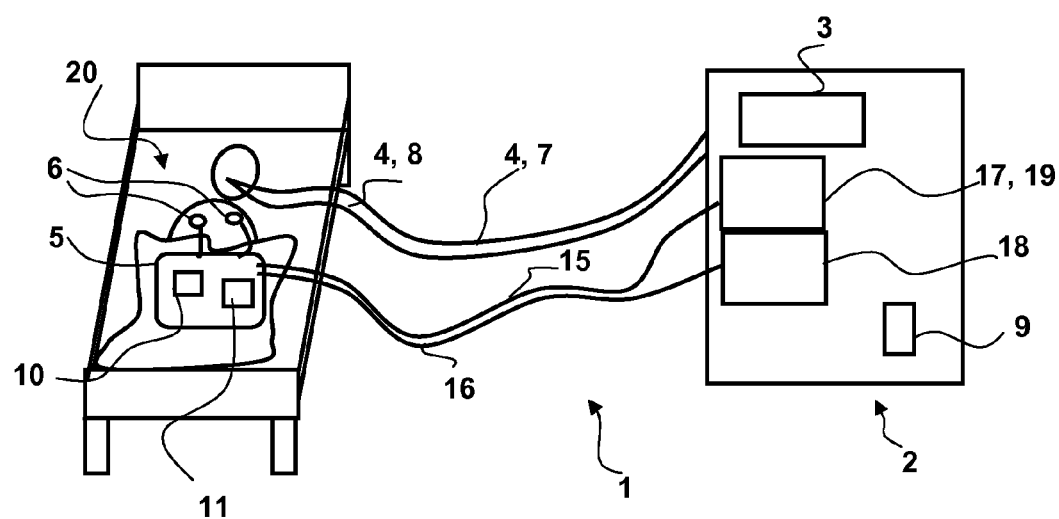
FIG. 1 is a highly simplified view of a first exemplary embodiment of a respirator or anesthesia system according to the invention.

Referring to the drawings in particular, respirators or respirator systems 1 are used to respirate patients 20 and anesthesia devices or anesthesia systems 1 are also used for the anesthesia of patients 20, besides for respiration. The respirator or anesthesia system 1 has a breathing air circulation system, i.e., the expiration gas expired by the patient 20 is reused for rebreathing as inspiration gas. The breathing air is sent by a gas delivery means 3 as a fan in a main unit 2 through gas lines 4 in a breathing air circulation system. The gas lines 4 are thus connected to the main unit 2. A first, inspiratory nonreturn valve and a second, expiratory nonreturn valve are arranged in the gas lines 4. An expiration gas line or an expiration tube 8 and an inspiration gas line or an inspiration tube 7 are formed as a result. A Y-piece, which sends the inspiration gas and expiration gas to and from a patient 20 being respirated, is connected at the end of the inspiration and expiration gas lines 7, 8. A $CO_2$ absorber, not shown, in the main unit 2 absorbs the carbon dioxide contained in the expiration gas. Furthermore, the inspiration gas is enriched with anesthetic (not shown) with an anesthetic reflector, not shown, in the main unit 2 and with an anesthetic dispensing unit. In addition, a mixture of oxygen and laughing gas is fed to the inspiration gas by means of a gas mixer, not shown, in the main unit. Oxygen and laughing gas are fed separately to the gas mixer by means of two valves.

The respirator or anesthesia system 1 comprises, furthermore, a measuring module 5 with two sEMG sensors 6, the sEMG sensors 6 being electrically connected to a measuring module 5 by means of an analog cable of a short length, for example, in the range of 3 cm to 15 cm. The two sEMG sensors 6 are located in the thoracic region on the skin of patient 20, i.e., the electric activity of the respiratory muscles is measured non-invasively by the sEMG sensors 6. The measuring module 5 has plug-type connectors, not shown, for connecting up to five pairs of sEMG sensors 6 (not shown). An analog-digital conversion unit 10 and a data processing unit 11 are arranged within a housing (not shown) of measuring module 5. The sEMG sensors 6 measure very weak currents with a voltage ranging from a few µV to about 100 µV, so that distortion of these low measured voltages may occur when sending these weak currents through a long analog cable over a greater distance. The voltages detected by the two sEMG sensors 6 are converted for this reason into digital signals with the analog-digital conversion unit 10 at a short distance from the sEMG sensors 6. The measuring module 5 is supplied with electric current from the main unit 2 by two power cables 15 (only one power cable 15 is shown). The power cables 15 in the measuring module 5 thus represent an energy supply unit. A DC-DC converter 17 acting as an induction unit with a primary coil and a secondary coil, not shown, is arranged in the main unit 2. Direct current is at first modulated, the modulated direct current is then transmitted from the primary coil to the secondary coil by means of induction, and the current induced in the secondary coil is subsequently converted again into direct current and sent through the two power cables 15 to the measuring module 5 for supplying the measuring module 5 with power. The power supply of the measuring module 5 is thus electrically and magnetically uncoupled from the main unit 2, so that interferences during the conversion of the measured analog currents into digital signals in the analog-digital conversion unit 10 are very weak.

The measuring module 5 is connected to the main unit 2 with a data cable 16 for transmitting the digital data generated in the analog-digital conversion unit 10 into the main unit 2. The data cable 16 is connected to a potential separation unit 18 in the main unit 2, and the digital data are transmitted by the potential separation unit 18 to a control means 9 in the main unit 2. the data cable 16 may be an electric cable for sending current or a fiber optic cable for optically transmitting data. The electric potential of the measuring module 5 is separated with the potential separation unit 18 from the electric potential of the main unit 2 to ensure that even in case of different electric potentials in the main unit 2 and the measuring module 5, no current resulting herefrom will flow through the data cable 16. The digital signals are analyzed in the control means 9 and controlled and/or regulated and the output of the gas delivery means 3 is controlled and/or regulated as a function of the digital signals, i.e., the electric potential difference from the respiratory muscle activity, which said potential difference is measured by the two sEMG sensors 6 on the skin surface.

Digital signals can be stored and processed in the data processing unit 11 and, furthermore, a measuring module 5 and hence also a patient 20 can be identified by the control unit 9 in case of using a plurality of measuring modules 5 for the main unit 2. In addition, check sums of the transmitted digital data and or control signals can be transmitted from the data processing unit 11 to the control means 9 in order to detect possible errors in the transmission from the measuring module 5 to the main unit 2 or to the control means 9. Incorrect respiration of the patient 20 due to data transmission errors shall thus be ruled out.

The measuring module 5 has, moreover, at least one sensor (not shown) for detecting a patient ground, i.e. the average electric potential of the patient 20. Differing from this, the patient ground can also be calculated from the average electric potential detected by the sEMG sensors 6. This sensor is a non-invasive sensor, which measures the electric potential on the skin surface. The electric potential in the measuring module 5 is controlled with the data processing unit such that the electric potential in the measuring module 5 corresponds essentially to the patient ground in order to prevent currents resulting herefrom in the analog cable for connecting the sEMG sensors 6 to the measuring module 5.

Figure 2:
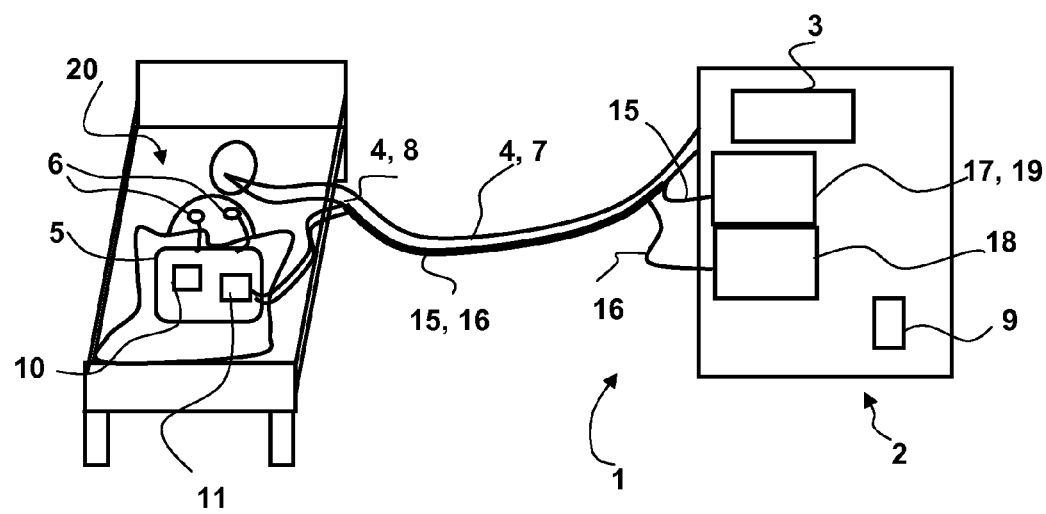
FIG. 2 is a highly simplified view of a second embodiment of the respirator or anesthesia system according to the invention.

FIG. 2 shows a second exemplary embodiment of the respirator or anesthesia system 1. Essentially only the differences from the first exemplary embodiment according to FIG. 1 will be described below. The power cable 15 and the data cable 16 for connecting the measuring module 5 to the main unit 2 are integrated in the inspiration tube 7 and or the expiration tube 8, so that the main unit 2 and the measuring module 5 are connected to one another by one line unit or one cable channel only for both the pneumatic and electric connection.

Figure 3:
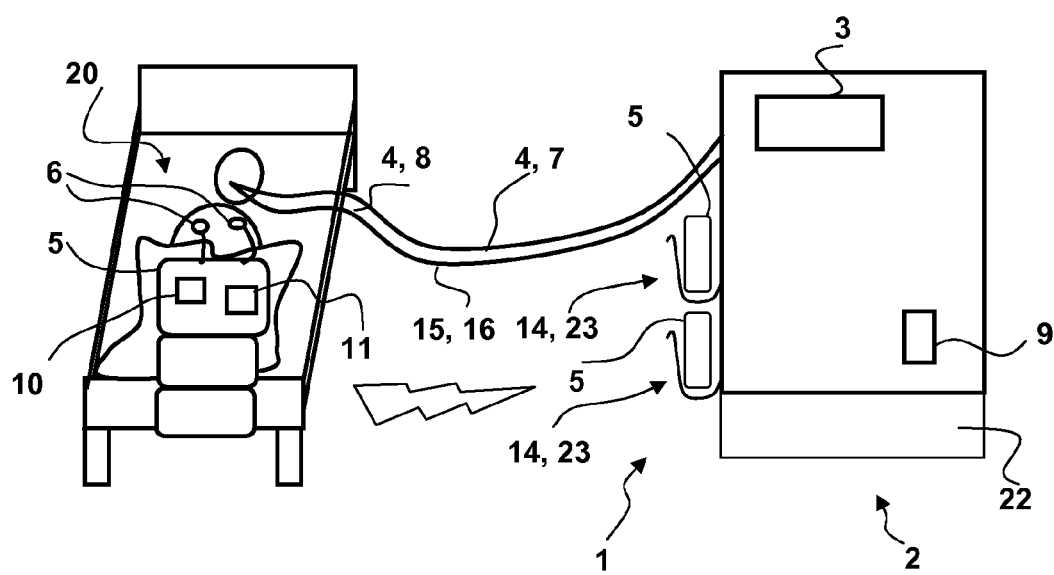
FIG. 3 is a highly simplified view of a third exemplary embodiment of the respirator or anesthesia system according to the invention.

FIG. 3 shows a third exemplary embodiment of the respirator or anesthesia system 1. Essentially only the differences from the first exemplary embodiment according to FIG. 1 will be described below. A battery 13 acting as an energy storage means 12 is installed in the measuring module 5 and is used to supply the measuring module 5 with electric energy. In addition, a transmitter 21 is installed in the measuring module 5 and a receiver 22 is installed in the main unit 2 for the wireless transmission of the digital signals from the measuring module 5 to the main unit 2 or to the control means 9. The digital signals concerning the electromyographic activity of the respiratory muscles are transmitted from the receiver 22 to the control means 9. A measuring module 5 can be identified by the control means 9 with a bidirectional wireless connection.

The respirator or anesthesia system 1 comprises two or three measuring modules 5, because one measuring module 5 is located at the patient for detecting the electromyographic activity of the respiratory muscles and transmitting the digital data, so that the battery 13 in the measuring module 5 at the patient 20 is discharged. The second or third measuring module 5 is arranged in a charging unit 14 as a parking holder 23 and is charged. The measuring module 5 at the patient 20 is replaced with a measuring module 5 charged in the charging unit 14 when the state of charge of the battery 13 drops below a preset state of charge. The measuring module 5 is provided with a central plug-in unit, not shown, with which all the sEMG sensors 6 arranged at the patient 20 can be connected to the measuring module 5. Thus, there also is no direct electric connection between the main unit 2 and the measuring module 5 at the patient 20, so that the measuring module 5 at the patient 20 is thus electrically and magnetically uncoupled from the main unit 2. The charging time of a measuring module 5 in the parking holder 23 is at most half the operating time of the measuring module 5 at the patient. The charging time is preferably ¼ or ⅙ of the operating time. An operating time of 24 hours compares, e.g., with a charging time of 4 hours. Digital data can also be transmitted during the charging of the measuring module 5 by means of contact elements, not shown, from the measuring module 5 into the control means 9, for example, concerning the history of the measuring module 5, charge cycles, number of operating hours and status information. The measuring module 5 can also be identified by the control means 9 by means of data in the data processing unit.

Figure 4:
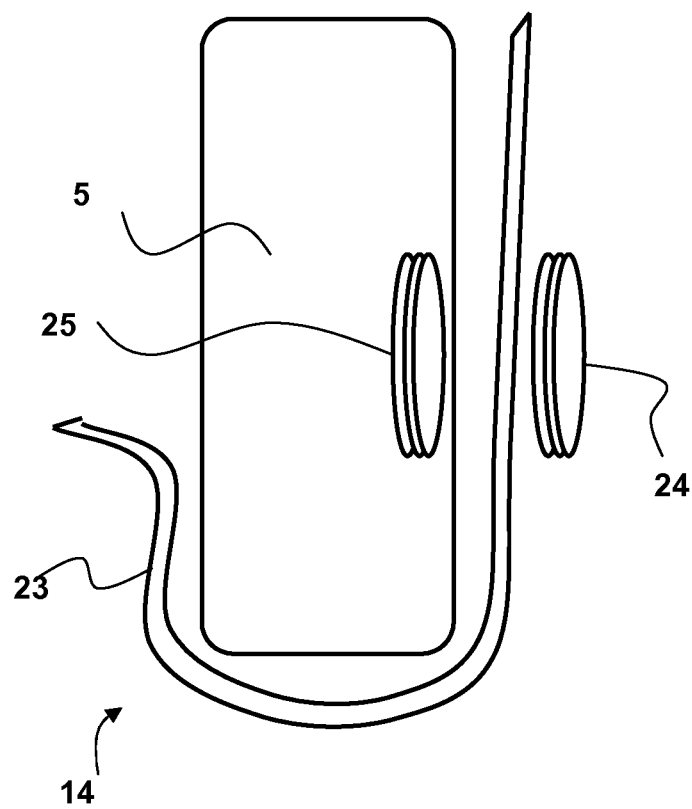
FIG. 4 is a schematic view showing a parking holder in a first exemplary embodiment of the respirator or anesthesia system according to FIG. 3.
Figure 5:
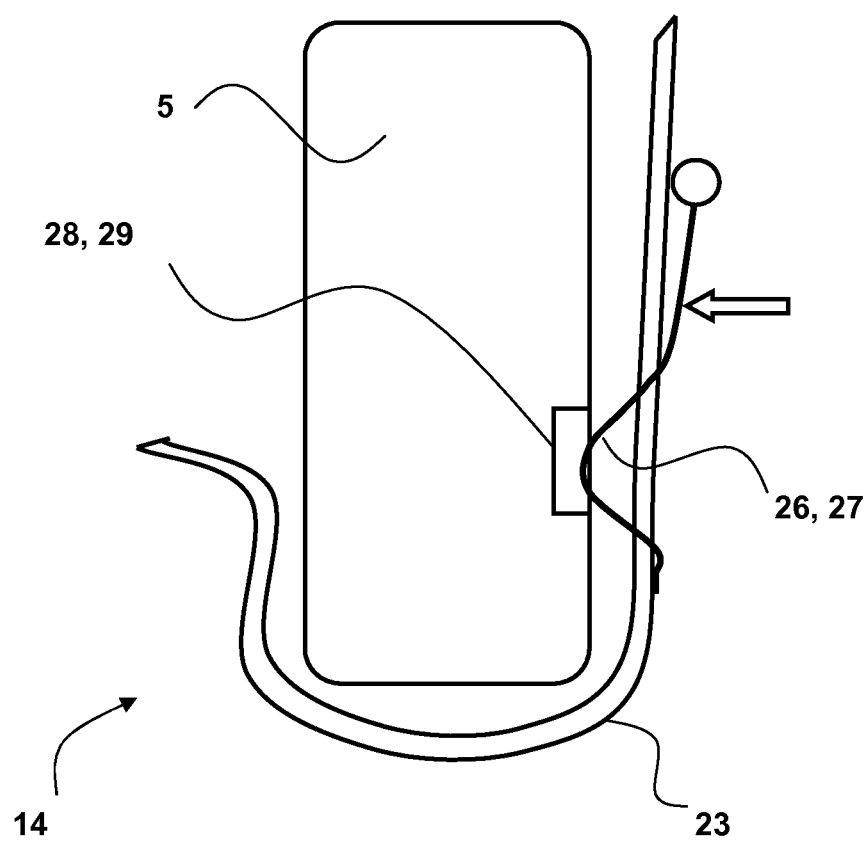
FIG. 5 is a schematic view showing the parking holder in a second exemplary embodiment of the respirator or anesthesia system according to FIG. 3.

FIGS. 4 and 5 show two exemplary embodiments for the charging unit 14. The energy or power is transmitted in the first exemplary embodiment according to FIG. 1 from a transmitter coil 24 at the main unit 2 to a receiver coil 25 in the measuring module 5 by means of electric induction in a contactless manner. The second exemplary embodiment (FIG. 5) of the charging unit 14 shows a contacted power transmission from the main unit 2 with a contact element 26 designed as a metal spring 27 at the main unit 2 and with a metal plate 29 as an opposite contact element 28. The charging unit 2 has two contact elements 26 each and the measuring module 5 is provided with two opposite contact elements 28. Electric current can thus be sent from the main unit 2 into the battery 13.

Figure 6:
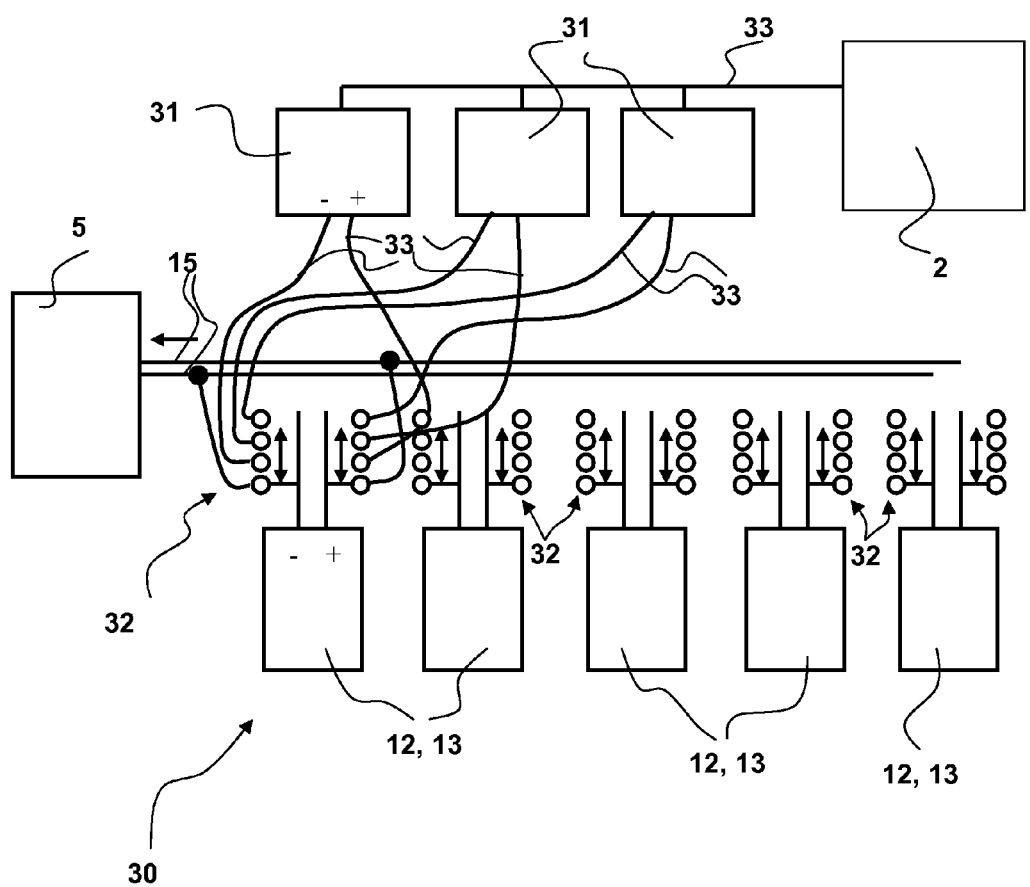
FIG. 6 is a schematic view showing a charging and switching unit of the respirator and anesthesia apparatus according to FIG. 7.
Figure 7:
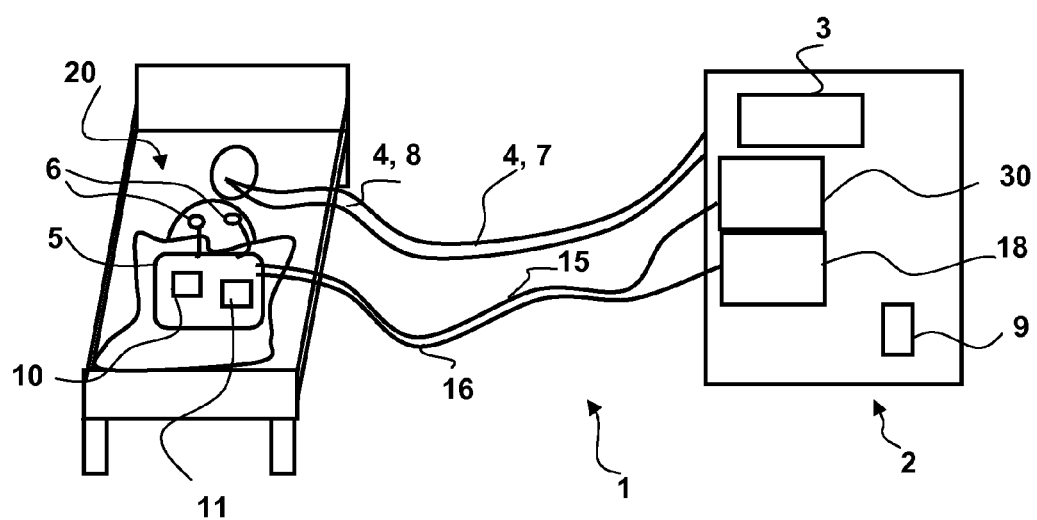
FIG. 7 is a highly simplified view of a fourth exemplary embodiment of the respirator or anesthesia system.

FIGS. 6 and 7 show a fourth exemplary embodiment of the respirator or anesthesia system 1. Essentially only the differences from the first exemplary embodiment according to FIG. 1 will be described below. A charging and switching unit 30 is arranged in the main unit 2. Batteries 13 are charged with charging parts 31 in the charging and switching unit 30. The charging parts 31 are connected by a charging cable 33 to the main unit 2 and to the batteries 13. In addition, the power cables 15, with which the power is sent from the batteries 13 into the measuring module 5, are led to the batteries 13. Switching units 32 at the batteries 13 are used to contact only one battery 13 to the measuring module 5 for supplying the measuring module 5 with power with one battery 13, and at least one other battery 13 is connected to a charging part 31 only for charging the at least one other battery 13. After a battery 13 has been discharged, the discharged battery 13 is electrically separated from the measuring module 5 with the switching unit 32 and another charged battery 13 is electrically connected to the measuring module 5. The discharged battery 13 is subsequently electrically connected to the charging part 31 and is charged. The batteries 13 are thus never connected simultaneously to both the measuring module 5 and the charging part 31 or the main unit 2, so that the measuring module 5 is electrically or magnetically uncoupled from the main unit 2. The charging and switching unit 30 may also be arranged in the measuring module 5 (not shown) instead of in the main unit 2.

On the whole, essential advantages are associated with the respirator or anesthesia system 1 according to the present invention. The gas delivery means 3 is operated as a function of the electromyographic activity of the respiratory muscles, which is measured with sEMG sensors 6, so that a disadvantageous invasive measurement is no longer necessary. The energy supply of the measuring module 5 is electrically and magnetically uncoupled from the main unit 2, so that no interferences due to an electric and magnetic coupling of the measuring module 5 with the main unit 2 can occur.

While specific embodiments of the invention have been shown and described in detail to illustrate the application of the principles of the invention, it will be understood that the invention may be embodied otherwise without departing from such principles.

What is claimed is:

1. A respirator or anesthesia system for respirating a patient, comprising:
    a gas delivery means;
    a gas line for forming a breathing air line system;
    an electromyographic (EMG) sensor, said EMG sensor non-invasively detecting an electromyographic muscle activity of breathing muscles on a skin surface of a patient to be respirated;
    a control means for controlling and/or regulating an output of said gas delivery means as a function of the detected muscle activity of the breathing muscles;
    a main unit comprising said gas delivery means;
    at least one measuring module connected to said EMG sensor;
    two energy storage means; and
    a charging and switching unit, said charging and switching unit supplying said at least one measuring module with energy such that at least one of said two energy storage means is electrically separated from an energy supply means of said main unit and said at least one of said two energy storage means is electrically connected with said at least one measuring module during a phase of discharge of said at least one of said two energy storage means and said at least one of said two energy storage means is electrically separated from said at least one measuring module and said at least one of said two energy storage means is electrically connected with said main unit during a phase of charging of said at least one of said two energy storage means.

2. A respirator or anesthesia system in accordance with claim 1, wherein another one of said two energy storage means is electrically connected to said main unit and said another one of said two energy storage means is electrically separated from said at least one measuring module via said charging and switching unit with said at least one of said two energy storage means in said phase of discharge, said another one of said two energy storage means being electrically connected with said at least one measuring module and said another one of said two energy storage means being electrically separated from said energy supply means of said main unit via said charging and switching unit with said at least one of said two energy storage means in said phase of charging.

3. A respirator or anesthesia system in accordance with claim 1, wherein said main unit comprises amain housing, said gas delivery means being arranged in said main housing, said at least one measuring module defining a portable assembly unit, said portable assembly unit being separate from said main unit.

4. A respirator or anesthesia system in accordance with claim 1, wherein said at least one measuring module comprises an analog-digital converter unit, said analog-digital converter unit converting analog electromyographic muscle activity detected by at least one EMG sensor into digital signals.

5. A respirator or anesthesia system in accordance with claim 1, wherein said at least one measuring module comprises a data processing unit and/or an energy supply unit.

6. A respirator or anesthesia system in accordance with claim 5, wherein said energy supply unit comprises at least one battery and/or at least one capacitor as one or more of said two energy storage means.

7. A respirator or anesthesia system in accordance with claim 6, wherein said main unit comprises a charging unit for one or more of said two energy storage means.

8. A respirator or anesthesia system in accordance with claim 5, wherein said energy supply unit comprises at least one power cable and said at least one power cable extends to said main unit for carrying electric current from said main unit to said at least one measuring module and current carried by said at least one power cable is carried at said main unit from said main unit to said at least one power cable with an induction unit with two coils by means of induction.

9. A respirator or anesthesia system in accordance with claim 1, wherein said at least one measuring module comprises at least one MMG sensor and/or at least one acceleration sensor and/or a microphone for detecting the muscle activity of the breathing muscles.

10. A respirator or anesthesia system in accordance with claim 1, wherein said breathing air line system comprises a breathing air circulation system.

* * * * *